(12) United States Patent
Lee

(10) Patent No.: US 8,070,719 B2
(45) Date of Patent: Dec. 6, 2011

(54) LOW COMPLIANT CATHETER TUBING

(75) Inventor: Jeong S. Lee, Diamond Bar, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 401 days.

(21) Appl. No.: 12/324,425

(22) Filed: Nov. 26, 2008

(65) Prior Publication Data

US 2010/0130927 A1    May 27, 2010

(51) Int. Cl.
*A61M 29/00* (2006.01)
*A61M 37/00* (2006.01)

(52) U.S. Cl. ............ 604/96.01; 604/103.06; 604/93.01; 604/103.13; 604/264

(58) Field of Classification Search .............. 156/250, 156/267, 292, 300; 604/915, 96.01–103.13, 604/264, 523–525
See application file for complete search history.

(56) References Cited

U.S. PATENT DOCUMENTS

| | | | |
|---|---|---|---|
| 4,952,357 A | 8/1990 | Euteneuer | |
| 5,112,304 A | 5/1992 | Barlow et al. | |
| 5,195,969 A | 3/1993 | Wang et al. | |
| 5,207,700 A | 5/1993 | Euteneuer | |
| 5,270,086 A | 12/1993 | Hamlin | |
| 5,290,306 A | 3/1994 | Trotta et al. | |
| 5,312,430 A | * 5/1994 | Rosenbluth et al. | |
| 5,358,486 A | 10/1994 | Saab | |
| 5,447,497 A | 9/1995 | Sogard et al. | |
| 5,478,320 A | 12/1995 | Trotta | |
| 5,499,980 A | 3/1996 | Euteneuer | |
| 5,512,051 A | 4/1996 | Wang et al. | |
| 5,556,383 A | 9/1996 | Wang et al. | |
| 5,587,125 A | 12/1996 | Roychowdhury | |
| 5,613,979 A | 3/1997 | Trotta et al. | |
| 5,620,649 A | 4/1997 | Trotta | |
| 5,755,690 A | 5/1998 | Saab | |
| 5,769,817 A | 6/1998 | Burgmeier | |
| 5,797,887 A | 8/1998 | Rosen et al. | |
| 5,833,657 A | 11/1998 | Reinhardt et al. | |
| 5,879,369 A | 3/1999 | Ishida | |

(Continued)

FOREIGN PATENT DOCUMENTS

EP    0420488    3/1991

(Continued)

OTHER PUBLICATIONS

U.S. Appl. No. 12/478,929, Jul. 18, 2011 Request for Continued Examination (RCE).*

(Continued)

*Primary Examiner* — Nicholas Lucchesi
*Assistant Examiner* — Leah Stohr
(74) *Attorney, Agent, or Firm* — Baker Botts LLP

(57) ABSTRACT

Balloon catheter comprises a shaft having a proximal end, a distal end, and an inflation lumen extending therein, and a balloon on the shaft which has an interior in fluid communication with the inflation lumen. The balloon is formed of a blend of polymeric materials comprising a transparent amorphous nylon having a Shore D duromcter hardness of not less than 77D and being not more than about 40% by weight of the blend, and a polyamide or a polyether block amide having a Shore D duromcter hardness of no more than 73D. An increase in radial diameter of the balloon above nominal pressure for one atmosphere of pressure is no greater than 0.025 mm/atm. A guidewire catheter is also provided.

25 Claims, 2 Drawing Sheets

U.S. PATENT DOCUMENTS

| | | | |
|---|---|---|---|
| 5,908,406 | A | 6/1999 | Ostapchenko et al. |
| 6,004,289 | A | 12/1999 | Saab |
| 6,004,339 | A | 12/1999 | Wijay |
| 6,059,751 | A | 5/2000 | Ostapchenko et al. |
| 6,071,266 | A | 6/2000 | Kelley |
| 6,086,556 | A | 7/2000 | Hamilton et al. |
| 6,124,007 | A | 9/2000 | Wang et al. |
| 6,132,824 | A | 10/2000 | Hamlin |
| 6,136,258 | A | 10/2000 | Wang et al. |
| 6,146,356 | A | 11/2000 | Wang et al. |
| 6,171,278 | B1 | 1/2001 | Wang et al. |
| 6,242,063 | B1 | 6/2001 | Ferrera et al. |
| 6,265,016 | B1* | 7/2001 | Hostettler et al. |
| 6,358,227 | B1 | 3/2002 | Ferrera et al. |
| 6,416,494 | B1 | 7/2002 | Wilkins |
| 6,500,148 | B1 | 12/2002 | Pinchuk et al. |
| 6,585,688 | B2 | 7/2003 | Ferrera et al. |
| 6,620,127 | B2 | 9/2003 | Lee et al. |
| 6,620,128 | B1 | 9/2003 | Simhambhatla |
| 6,645,422 | B2 | 11/2003 | Jung, Jr. et al. |
| 6,673,302 | B2 | 1/2004 | Wang et al. |
| 6,695,809 | B1 | 2/2004 | Lee |
| 6,756,094 | B1 | 6/2004 | Wang et al. |
| 6,796,958 | B2* | 9/2004 | Chen et al. ................. 604/96.01 |
| 6,796,960 | B2 | 9/2004 | Cioanta et al. |
| 6,835,189 | B2 | 12/2004 | Musbach et al. |
| 6,875,197 | B1 | 4/2005 | Simhambhatia et al. |
| 6,911,038 | B2 | 6/2005 | Mertens et al. |
| 6,946,092 | B1 | 9/2005 | Bertolino et al. |
| 6,951,675 | B2 | 10/2005 | Chin et al. |
| 7,026,026 | B2 | 4/2006 | Ferrera et al. |
| 7,029,732 | B2 | 4/2006 | Wang et al. |
| 7,074,206 | B2 | 7/2006 | Lee et al. |
| 7,112,357 | B2 | 9/2006 | Miller et al. |
| 7,147,817 | B1 | 12/2006 | Lim et al. |
| 7,195,638 | B1 | 3/2007 | Sridharan |
| 7,335,185 | B2 | 2/2008 | Tang et al. |
| 2002/0018866 | A1 | 2/2002 | Lee et al. |
| 2002/0165523 | A1 | 11/2002 | Chin et al. |
| 2003/0009151 | A1* | 1/2003 | Wang ............................. 604/526 |
| 2003/0064130 | A1* | 4/2003 | Blair et al. ...................... 426/49 |
| 2003/0139762 | A1* | 7/2003 | Lee |
| 2004/0064130 | A1* | 4/2004 | Carter ............................ 604/523 |
| 2004/0131808 | A1* | 7/2004 | Schoenle et al. ............. 428/35.7 |
| 2004/0170782 | A1 | 9/2004 | Wang et al. |
| 2004/0173935 | A1 | 9/2004 | Lim et al. |
| 2004/0191443 | A1 | 9/2004 | Hamlin |
| 2005/0043679 | A1 | 2/2005 | Devens et al. |
| 2005/0124976 | A1 | 6/2005 | Devens, Jr. et al. |
| 2005/0131445 | A1 | 6/2005 | Holman et al. |
| 2005/0186370 | A1 | 8/2005 | Hamilton et al. |
| 2005/0228429 | A1 | 10/2005 | Burgmeier et al. |
| 2005/0238833 | A1 | 10/2005 | Wang et al. |
| 2005/0277878 | A1* | 12/2005 | Lee |
| 2006/0165926 | A1 | 7/2006 | Weber |
| 2007/0060863 | A1 | 3/2007 | Goeken et al. |
| 2007/0142771 | A1 | 6/2007 | Durcan |
| 2007/0167973 | A1 | 7/2007 | Stupecky et al. |
| 2007/0191813 | A1* | 8/2007 | Chen |
| 2007/0240817 | A1* | 10/2007 | Strong et al. ............... 156/304.3 |
| 2008/0065188 | A1 | 3/2008 | Pallazza |
| 2008/0262470 | A1 | 10/2008 | Lee et al. |
| 2009/0264822 | A1* | 10/2009 | Johnson |
| 2010/0010439 | A1* | 1/2010 | Burgmeier et al. |

FOREIGN PATENT DOCUMENTS

| | | |
|---|---|---|
| EP | 0962227 | 12/1999 |
| JP | 2005-167638 | 6/2005 |
| WO | 99/13924 A2 | 3/1999 |
| WO | 0151115 | 7/2001 |
| WO | WO 0236196 * | 5/2002 |
| WO | 2005021083 | 3/2005 |
| WO | 2006126311 | 11/2006 |

OTHER PUBLICATIONS

U.S. Appl. No. 12/478,929, filed Jun. 5, 2009.
U.S. Appl. No. 12/479,700, filed Jun. 5, 2009.
U.S. Appl. No. 12/478,929, Mar. 4, 2011 Final Office Action.
U.S. Appl. No. 12/478,929, Dec. 9, 2010 Response to Non-Final Office Action.
U.S. Appl. No. 12/478,929, Jul. 9, 2010 Non-Final Office Action.
U.S. Appl. No. 12/479,700, Apr. 27, 2011 Response to Non-Final Office Action.
U.S. Appl. No. 12/479,700, Oct. 27, 2010 Non-Final Office Action.
International Search Report for PCT/US2010/037313; International Filing Date: Jun. 3, 2010.

* cited by examiner

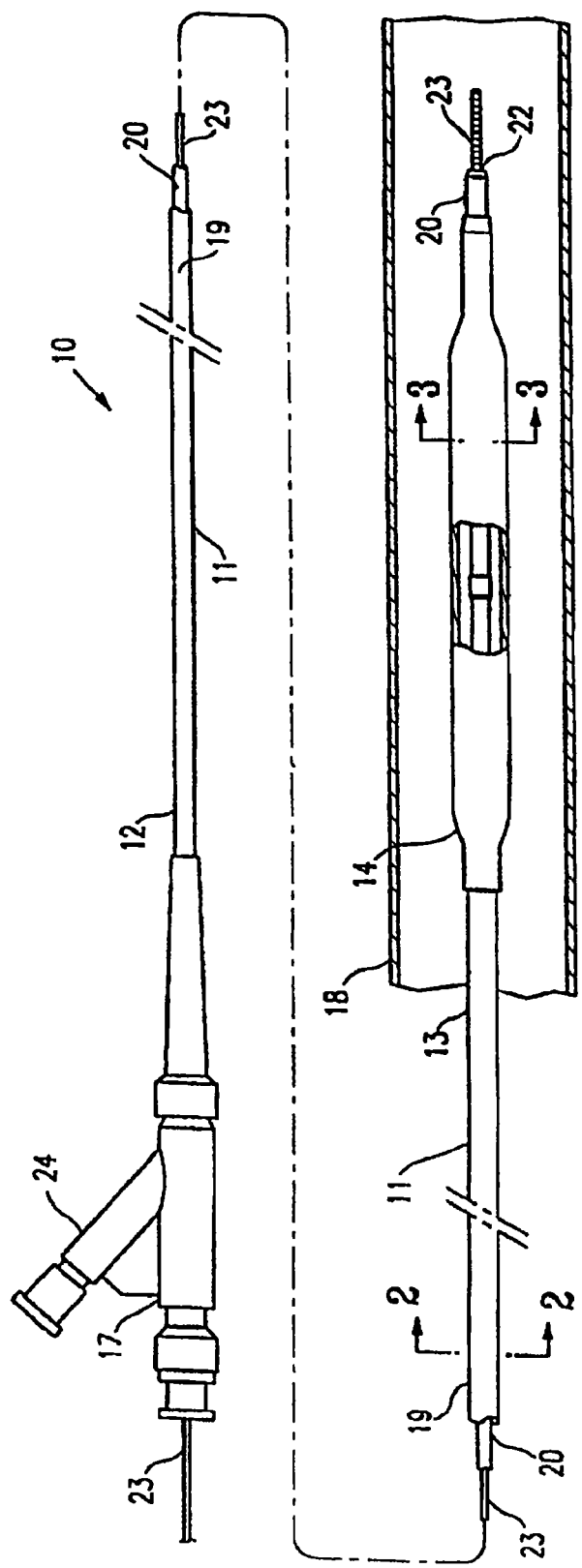

LOW COMPLIANT CATHETER TUBING

BACKGROUND

The invention relates to the field of intravascular catheters, and more particularly to a balloon catheter or other catheter component, such as a guidewire enclosure, that would benefit from the properties of the materials disclosed herein.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. The rate of expansion of the balloon for a given pressure is an important consideration in the design of the dilation catheter, as greater than anticipated expansion of the balloon against the vessel wall can cause trauma to the vessel wall. After the balloon is finally deflated, blood flow resumes through the dilated artery and the dilatation catheter can be removed from the patient's artery.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy. The balloon compliance is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range. However, non-compliant balloons generally have relatively low flexibility and softness, making it more difficult to maneuver through various body lumens. Heretofore the art has lacked an optimum combination of strength, flexibility, and compliance, and particularly a low to non-compliant balloon with high flexibility and softness for enhanced trackability.

Therefore, what has been needed is a catheter balloon with relatively low compliance, and with improved ability to track the patient's vasculature and cross lesions therein. The present invention satisfies these and other needs.

SUMMARY OF THE INVENTION

The softness and flexibility of a balloon is a function of the flexural modulus of the polymeric material of the balloon, so that a balloon material having a higher Shore D durometer hardness, which yields a stronger and stiffer balloon, has a higher flexural modulus. Conversely, a balloon material having a lower Shore D durometer hardness, which thus provides a soft and flexible balloon, has a lower flexural modulus. The present invention is directed to a low compliance catheter balloon formed with a combination of at least two polyamides, a high durometer hardness material and a lower durometer hardness material. The balloon or other catheter component of the invention is preferably noncompliant or low-compliant. The term "noncompliant" should be understood to mean a balloon with compliance of not greater than about 0.03 millimeters/atmospheres (mm/atm). The term "low compliant" should be understood to mean a balloon with a compliance not greater than about 0.045 (mm/atm). In contrast, compliant balloons typically have a compliance of greater than about 0.045 mm/atm.

The balloon can be made from a blend of the two polyamides, or a co-extrusion of the two polyamides with an inner layer and an outer layer. The first polyamide has a Shore D durometer hardness of more than 77D, and can be preferably selected from various transparent amorphous nylons having segment such as an aliphatic segment, an aromatic segment, or a cycloaliphatic segment. The second polyamide has a lower durometer hardness than the first polyamide, and preferably less than 73D, and can be a block copolymer of nylon and polytetramethylene glycol (i.e. a copolyamide). Both polyamides preferably have the same amide block or segment, e.g. nylon 12, nylon 11, or nylon 6,6.

Where blended, the ratio of the high hardness polyamide to low hardness polyamide is preferably has at least sixty percent (60%) low hardness polyamide and forty percent (40%) high hardness polyamide, and more preferably eighty percent (80%) low hardness polyamide and twenty percent (20%) high hardness polyamide, and even more preferably ninety percent (90%) or more of the low hardness polyamide and ten percent (10%) or less of the high hardness polyamide. When co-extruded, the layer thickness of first polyamide is preferably less than 20% of the total wall thickness of the extruded tubing.

The low hardness polyamide or copolyamide is typically semi-crystalline having crystalline region and amorphous region. The amorphous region generally has a lower density than the crystalline region and generally has lower modulus, resulting in higher compliance in the amorphous region compared to crystalline region. This higher compliance in the amorphous region affects the overall modulus of the material and causes the material to be more compliant. If amorphous region can be reinforced by a higher modulus compatible material, the overall strength and modulus can be increased and compliance can be decreased. The present invention creates a balloon where the amorphous region of the lower durometer polyamide or copolyamide is reinforced by adding small amounts of a higher modulus amorphous material, thereby delaying the response of the amorphous region and increasing the overall modulus and strength of the material.

The preferred high hardness material is a new nylon referred to as transparent amorphous nylon, such as selected nylon 12. The transparent amorphous nylon preferably has either an aliphatic segment, an aromatic segment, or a cycloaliphatic segment.

The balloon of the invention is formed by extruding a tubular product formed from the blend of the first polymeric component and at least a second polymeric component. Alternatively, the two polymeric components can be co-extruded separately to create a tubing having an outer layer and an inner layer of the two materials. In a presently preferred embodiment, the balloon is formed by expanding an extruded tubular product in a balloon mold. Axial tension may be applied to the balloon during expansion, and the balloon may be cooled under pressure and tension between blowing steps. In one embodiment, the balloon is formed by expanding the extruded tubular product in a series of successively larger balloon molds.

Various designs for balloon catheters well known in the art may be used in the catheter system of the invention. For example, conventional over-the-wire balloon catheters for angioplasty or stent delivery usually include a guidewire receiving lumen extending the length of the catheter shaft from a guidewire port in the proximal end of the shaft. Rapid exchange balloon catheters for similar procedures generally include a short guidewire lumen extending to the distal end of the shaft from a guidewire port located distal to the proximal end of the shaft.

The balloon catheter of the invention has improved performance due to the flexibility, strength, and controlled expansion (compliance) of the balloon. The polymeric blend provides the surprising result of a balloon having a low compliance, for controlled balloon expansion, and having relatively high flexibility and softness, for excellent ability to track the patient's vasculature and cross lesions. These and other advantages of the invention will become more apparent from the following detailed description of the invention and the accompanying exemplary drawings.

BRIEF DESCRIPTION OF THE DRAWINGS

FIG. 1 is an elevated view partially in section of a balloon catheter which embodies features of the invention, showing the balloon in an expanded state;

FIG. 2 is a transverse cross sectional view of the balloon catheter of FIG. 1 taken along lines 2-2;

FIG. 3 is a transverse cross sectional view of the balloon catheter of FIG. 1 taken along lines 3-3.

DETAILED DESCRIPTION OF THE PREFERRED EMBODIMENTS

Figure 4:
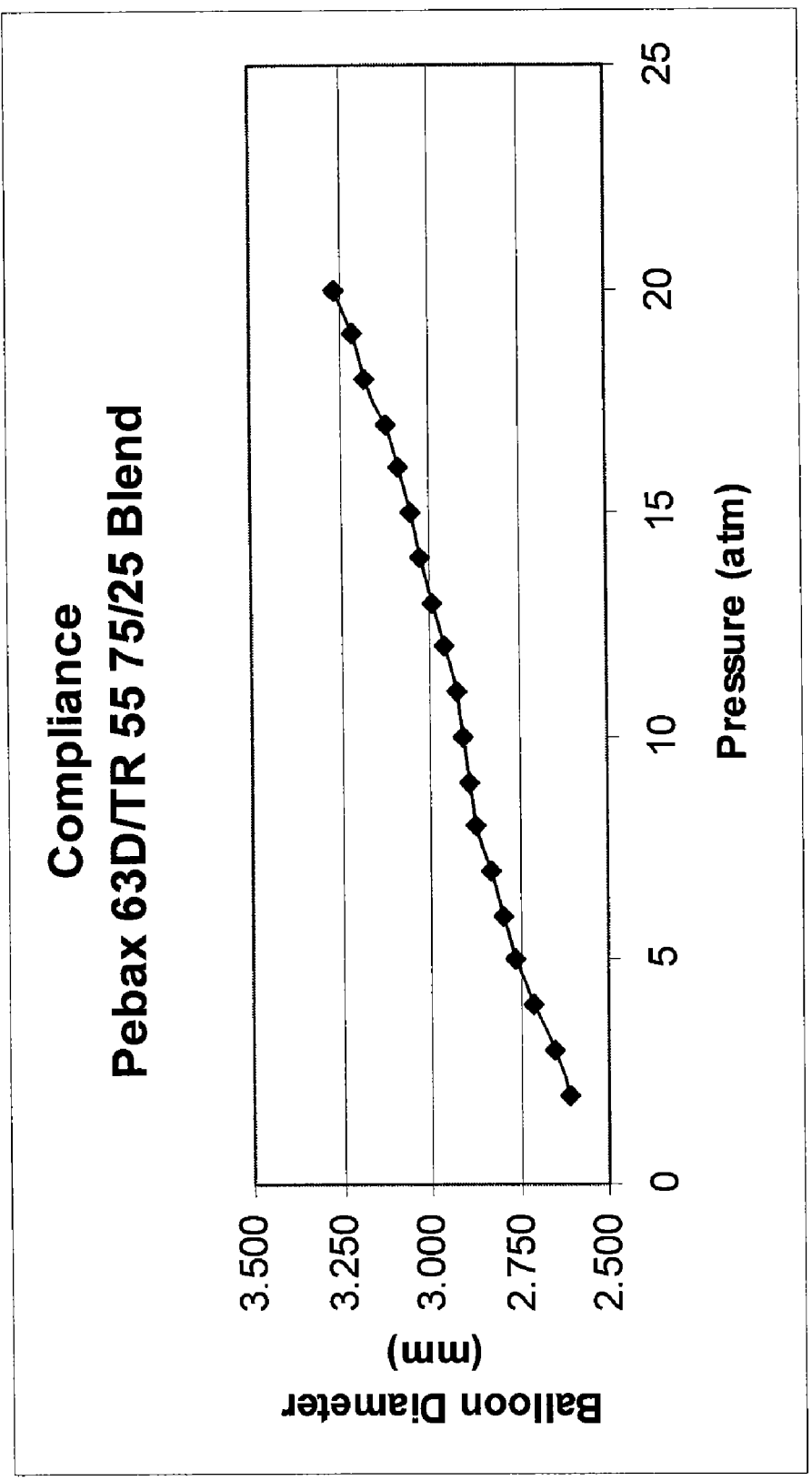
FIG. 4 is a graph of the compliance of the catheter balloon using a first preferred blend of materials.

In angioplasty balloons, an object is to apply a high pressure to the interior wall of the lumen to compress the plaque and/or to fully expand the stent. This relies on a robust balloon with a sturdy out wall and a high pressure capability. The compliance of the balloon, i.e., the expansion of the balloon as a function of internal pressure, is preferably low or flat to more accurately control the amount of pressure applied to the arterial wall. However, the deliverability of the balloon is also a factor, especially where tortuous body lumens are involved. Stiff balloons (i.e., high modulus materials) tend to have poor flexibility and lack the maneuverability to navigate the various body lumens, and thus make poor choices for catheter balloons. Conversely, flexible balloons (low modulus materials) that have high compliance are poorly suited to apply a precise known pressure on the arterial wall due to a high expansion rate per applied pressure. The goal is thus to increase the rupture strength by adding the high modulus material such as nylon to the softer polyamide material.

Soft polyamide materials such as Pebax® are semi-crystalline polymers and usually include an amorphous segment. The amorphous segment has a lower density than the crystalline structure and thus is weaker in general than crystalline segments. If the amorphous segment can be reinforced by adding a small amount of a higher modulus material the response of the amorphous segment can be delayed and the overall strength of the material can be strengthened. The high modulus material preferably has a Shore D durometer hardness of 77D or more. Suitable materials include transparent amorphous nylon such as nylon 12, and more preferably a nylon 12 with a aliphatic segment, an aromatic segment, or a cycloaliphatic segment. These nylons are transparent amorphous because they are essentially amorphous, lacking the crystalline structure of other more conventional nylon 12. The aliphatic segment, aromatic segment, or cycloaliphatic segment does not crystallize with the main chain, disrupting the formation of longer crystalline chains in the polymer. The amorphous segment of the transparent amorphous nylon 12 combines with the amorphous segment of the Pebax to strengthen the Pebax by enhancing the weakest link in the chain, thereby increasing the overall strength of the polymer. The benefit is realized with small amounts of the high modulus material, with as little as 40% to 10% of the high modulus material combining with 60% to 90% of the low strength Pebax.

FIG. 1 illustrates a balloon catheter which embodies features of the invention. The catheter 10 of the invention generally comprises an elongated catheter shaft 11 having a proximal section, 12 a distal section 13, an inflatable balloon 14 formed of a blend of polymeric materials on the distal section 13 of the catheter shaft 11, and an adapter 17 mounted on the proximal section 12 of shaft 11. In FIG. 1, the catheter 10 is illustrated within a patient's body lumen 18, prior to expansion of the balloon 14.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

FIGS. 2 and 3 show transverse cross sections of the catheter shaft 11 and balloon 14, respectively, illustrating the guidewire receiving lumen 22 of the guidewire's inner tubular member 20 and inflation lumen 21 leading to the balloon interior 15. The balloon 14 can be inflated by radiopaque fluid introduced at the port in the side arm 24 into inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

Non-compliant or low-compliant balloon 14 is formed of a blend of a first polyamide having a Shore D durometer hardness greater than 77D and a copolyamide of lower durometer hardness, preferably less than 73D. A preferred polyamide having a Shore D durometer hardness greater than 77D is an amorphous polyamide such as EMS TR 55 (transparent amorphous nylon 12), Arkema Rilsan G110 (transparent amorphous nylon 12), or Cristamid MS 110 (transparent amorphous nylon 12). The polyamide is preferably includes a cycloaliphatic segment, an aromatic segment, or an aliphatic segment. Such polyamides are also referred to as transparent polyamide. The preferred copolyamide material for forming the polymeric blend for the balloon is Pebax, and more preferably Pebax 72D, Pebax 70D or Pebax 63D. Alternatively, the copolyamide of lower durometer hardness is preferably a block copolymer of nylon 12 and polytetramethylene glycol.

The flexural modulus of the polyamide is preferably greater than 1700 MPa and the flexural modulus of the copolyamide is less than 850 MPa. The tensile strength at break of both polyamides is at least 50 MPa, and elongation at break of both polyamides is at least 150%.

In a presently preferred embodiment, the balloon of the invention is formed by blow molding an extruded tubular product formed of a blend of the first and second polyether block amide polymeric materials. The extruded tubular product is expanded to the final working diameter of the balloon in a balloon mold. The balloon may be heat set in the mold. In one alternate embodiment, the balloon is blown in a series of successively larger balloon molds. Thus, the extruded tubular product is placed in a first mold and the outer diameter of the tubular product is expanded at elevated pressure and temperature to a first outer diameter. The balloon is then placed in a second, larger mold, and expanded at elevated pressure and temperature to a second outer diameter larger than the first outer diameter. The number of successively larger molds used to expand the balloon may vary depending on the balloon material and size. To form a 3.0 mm outer diameter (OD) balloon, the tubular member is expanded in a first mold to an OD of about 2.0 to about 2.5 mm, and then expanded in a second mold to the working diameter of 3.0 mm. Preferably, axial tension is applied to the balloon during expansion, and the balloon is cooled in the mold, under pressure and tension, between blowing steps. However, the balloon of the invention is preferably produced by conventional techniques for producing catheter inflatable members in which the extruded tubular product is expanded in a single mold to the working diameter.

The balloon 14 has sufficient strength to withstand the inflation pressures needed to inflate the balloon. The tensile strength of an American Standard Testing Method (ASTM) "dog-bone" sample cut from a compression molded sheet of material is at least about 8,000 psi to about 9,000 psi. The hoop strength, e.g. the product of the burst pressure and the balloon diameter, divided by two times the balloon wall thickness, of a 3.0 mm balloon of the invention is about 22,000 psi to about 32,000 psi.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 4 cm, preferably about 0.8 cm to about 4.0 cm, and is typically about 2.0 cm. In an expanded state, at nominal pressure of about 8 to about 10 atm, the balloon diameter is generally about 0.06 in (1.5 mm) to about 0.20 in (5.0 mm). and the wall thickness is about 0.0006 in (0.015 mm) to about 0.001 in (0.025 mm), or a dual wall thickness of about 0.025 mm to about 0.056 mm. The burst pressure is typically about 20 to 26 atm, and the rated burst pressure is typically about 18 atm.

In a presently preferred embodiment, the balloon 14 may include wings, which may be folded into a low profile configuration (not shown) for introduction into and advancement within the patient's vasculature. When inflating the balloon to dilate a stenosis, the catheter 10 is inserted into a patient's vasculature to the desired location, and inflation fluid is delivered through the inflation lumen 21 to the balloon 14 through the inflation port 24. The semi-compliant or noncompliant balloon 14 expands in a controlled fashion with limited radial expansion, to increase the size of the passageway through the stenosed region. Similarly, the balloon has low axial growth during inflation, to a rated burst pressure of about 14 atm, of about 5 to about 10%. The balloon is then deflated to allow the catheter to be withdrawn. The balloon may be used to deliver a stent (not shown), which may be any of a variety of stent materials and forms designed to be implanted by an expanding member, see for example U.S. Pat. No. 5,514,154 (Lau et al.) and U.S. Pat. No. 5,443,500 (Sigwart), incorporated herein in their entireties by reference.

EXAMPLE 1

A blended composition of 75% Pebax 63D and 25% EMS TR 55 (transparent amorphous nylon) was constructed into ten sample catheter balloons according to the present invention, which produced an average working pressure range of eight to nine atmospheres for a 2.75 mm balloon. At five atmospheres, the balloon is about 2.75 mm (nominal diameter) and at thirteen atmospheres the balloon has grown radially roughly 0.25 mm to 3.00 mm (quarter size diameter). As shown in FIG. 4, this results in a compliance performance that is flatter in the operating range of the balloon, a desired characteristic. The balloon in Example 1 has a compliance of about 0.023 mm/atm between 5 atmospheres and 18 atmospheres, i.e., from nominal to the rated burst pressure of the balloon, where the nominal pressure is the pressure required to expand the balloon to its working diameter, and the rated burst pressure, calculated from the average rupture pressure, is the pressure at which 95% of the balloons can be pressurized to without rupturing.

The benefit of the present invention is blending amorphous (transparent amorphous) nylon to Pebax to reinforce the amorphous region (due to exclusion into amorphous region during crystallization) of semi crystalline region of Pebax or nylon. This results in a higher tensile strength (~11,000 psi) compared to nylon 12 or Pebax (7,500~8,200 psi) to yield a higher rupture balloon with same wall thickness; higher flexural modulus (~270,000 psi) compared to nylon 12 or Pebax (60,000~230,000 psi) to produce a flatter compliance balloon with same wall thickness; enhanced dimensional stability during shelf storage due to the higher glass transition temperature (155° C.) compared to nylon 12 or Pebax (45~55° C.); and lower processing temperature facilitating the thermal bonding process.

U.S. Pat. No. 7,074,206 co-invented by the inventor of the present invention and assigned to the assignee of the present application, incorporated fully herein by reference, discloses a catheter balloon where Pebax 70D is blended with a softer Pebax 63D to add flexibility to the Pebax 70D balloon. Approximately 40% by weight of the higher modulus Pebax 70D is blended with 60% by weight of the softer Pebax, to yield a balloon with a working pressure range of 6 atm (pressure at quarter size-nominal pressure). The present invention, for example the blend described above, shows that, with 25% TR55 (amorphous nylon) blended into Pebax 63D, the working pressure range for a 2.75 mm balloon is now 8~9 atm (nominal pressure 5 atm and quarter size at 13~14 atm), with a flatter compliance. Thus, the present invention yields a stronger balloon with a flatter compliance without sacrificing flexibility.

In addition to balloons, the blended composition has usefulness as other parts of the catheter, such as the guidewire enclosure 20 of FIGS. 1-3. The inner member of the multi-layered tubing can have a lubricious inner layer (HDPE. UHMWPE, and the like) with bonding mid layer and polymer blend outer layer. Like the catheter balloon, the blend is comprised of one polymer having a Shore D durometer greater than 77 and another polymer having lower durometer, preferably less than 73D. Both polyamides preferably have same amide block or segment, i.e. one type of amide (nylon) block, solely comprised of nylon 12, nylon 11, nylon 6, or nylon 6, 6 but not combination of these.

The polyamide having Shore D durometer greater than 77D is preferably amorphous polyamide selected from polyamide such as EMS TR 55 (transparent amorphous nylon 12), Arkema Rilsan G110 (transparent amorphous nylon 12), or Cristamid MS 110 (transparent amorphous nylon 12). This polyamide is preferably a copolyamide comprising cycloaliphatic, and/or aromatic, and/or aliphatic segment. The other copolyamide of lower durometer is preferably a block copolymer of nylon 12 and polytetramethylene glycol, such as Pebax 72D, Pebax 70D or Pebax 63D.

The high durometer polymer serves to increase resistance to collapse of the tubing and provides enhanced pushability while the lower durometer polymer provides flexibility and kink resistance. Although it is preferred to have blends of high miscibility, the blend ratio is such that the lower durometer polymer forms a "virtual" continuous phase while the higher durometer polymer forms "virtual" reinforcement.

I claim:

1. A balloon catheter, comprising:
   a shaft having a proximal end, a distal end, and an inflation lumen extending therein; and
   a balloon on the shaft which has an interior in fluid communication with the inflation lumen, and which is formed of a blend of polymeric materials comprising a transparent amorphous nylon having a Shore D durometer hardness of not less than 77D and being not more than about 40% by weight of the blend, and a polyamide or a polyether block amide having a Shore D durometer hardness of no more than 73D;
   wherein an increase in radial diameter of the balloon above nominal pressure for one atmosphere of pressure is no greater than 0.025 mm/atm.

2. The balloon catheter of claim 1 wherein the transparent amorphous nylon is not more than about 20% by weight of the blend.

3. The balloon catheter of claim 1 wherein the transparent amorphous nylon is not more than about 10% by weight of the blend.

4. The balloon catheter of claim 1 wherein the transparent amorphous nylon is comprised of nylon 12.

5. The balloon catheter of claim 1 wherein the transparent amorphous nylon has an aliphatic segment.

6. The balloon catheter of claim 1 wherein the transparent amorphous nylon has an aromatic segment.

7. The balloon catheter of claim 1 wherein the transparent amorphous nylon has a cycloaliphatic segment.

8. The balloon catheter of claim 1 wherein the polyamide or polyether block amide is a semi-crystalline polymer.

9. The balloon catheter of claim 1 wherein an amorphous segment of the transparent amorphous nylon combines with an amorphous segment on the polyamide or polyether block amide.

10. The balloon catheter of claim 1 wherein the polyether block amide is a copolyamide of nylon 12 and polytetramethylene glycol.

11. The balloon catheter of claim 1 wherein a flexural modulus of the transparent amorphous nylon is not less than 1700 MPa and the flexural modulus of the polyamide or polyether block amide is not more than 850 MPa.

12. The balloon catheter of claim 1 wherein a tensile strength at break of the transparent amorphous nylon or the polyamide or polyether block amides is at least 50 MPa.

13. A guidewire catheter, comprising:
   a main shaft having a proximal end, a distal end, and an inflation lumen extending therein; and
   a guidewire shaft disposed at least partially within the main shaft, the guidewire shaft formed of a blend of polymeric materials comprising a transparent amorphous nylon having a Shore D durometer hardness of not less than 77D and being not more than about 40% by weight of the blend, and a polyether block amide having a Shore D durometer hardness of no more than 73D.

14. The guidewire catheter of claim 13 wherein the transparent amorphous nylon is not more than about 20% by weight of the blend.

15. The guidewire catheter of claim 13 wherein the transparent amorphous nylon is not more than about 10% by weight of the blend.

16. The guidewire catheter of claim 13 wherein the transparent amorphous nylon is nylon 12.

17. The guidewire catheter of claim 13 wherein the transparent amorphous nylon has an aliphatic segment.

18. The guidewire catheter of claim 13 wherein the transparent amorphous nylon has an aromatic segment.

19. The guidewire catheter of claim 13 wherein the transparent amorphous nylon has a cycloaliphatic segment.

20. The guidewire catheter of claim 15 wherein the polyether block amide is a semi-crystalline polymer.

21. The guidewire catheter of claim 13 wherein the polyether block amide includes an amorphous segment.

22. The guidewire catheter of claim 21 wherein the amorphous segment combines with an amorphous segment of the transparent amorphous nylon.

23. The guidewire catheter of claim 13 wherein the polyether block amide is a copolyamide of nylon 12 and polytetramethylene glycol.

24. The guidewire catheter of claim 13 wherein the transparent amorphous nylon has a flexural modulus of is not less than 1700 MPa and the polyether block amide has a flexural modulus is not more than 850 MPa.

25. The guidewire catheter of claim 13 wherein a tensile strength at break of each of the transparent amorphous nylon and of the polyether block amide is at least 50 MPa.

* * * * *